United States Patent [19]

Busse

[11] 4,425,439

[45] Jan. 10, 1984

[54] UPFLOW DRYING OF REGENERATED ETHYLENE OXIDE CATALYSTS

[75] Inventor: Paul J. Busse, Omaha, Nebr.

[73] Assignee: InterNorth, Inc., Omaha, Nebr.

[21] Appl. No.: 392,537

[22] Filed: Jun. 28, 1982

[51] Int. Cl.$^3$ .................... B01J 23/96; C07D 301/10
[52] U.S. Cl. .......................................... 502/25; 34/22; 502/34; 549/534
[58] Field of Search .................. 252/414, 412, 411 R, 252/410; 549/534; 34/22, 30

[56] References Cited

U.S. PATENT DOCUMENTS 4,186,106 1/1980 Rebsdat et al. ..................... 252/414

FOREIGN PATENT DOCUMENTS 2362846 3/1978 France ........................... 252/411 R

*Primary Examiner*—P. E. Konopka
*Attorney, Agent, or Firm*—Donald F. Haas

[57] ABSTRACT

The performance of silver-based catalyst used for the direct oxidation of ethylene to ethylene oxide is improved by regeneration in which from 1 to 1,000 parts per million of a regenerate is added to the catalyst in solution and the solvent is removed by drying the catalyst with a upflow of inert gas through the catalyst at ambient temperature and pressure.

16 Claims, No Drawings

UPFLOW DRYING OF REGENERATED ETHYLENE OXIDE CATALYSTS

BACKGROUND OF THE INVENTION

This invention relates to the regeneration of supported silver catalysts. More particularly, the invention relates to an improved method for drying such catalysts which have been regenerated by treating them with solutions of one or more alkali metal, especially cesium and/or rubidium, salts.

Supported silver-based catalysts have been used industrially for many years for the oxidation of ethylene to ethylene oxide with oxygen or air. Most of the ethylene which is reacted is converted into ethylene oxide on the silver-impregnated catalyst support material and the remainder of the ethylene is converted almost exclusively to carbon dioxide and water. The goal is to react as much ethylene as is possible, i.e. high productivity, such that the greater amount of the ethylene is converted to ethylene oxide, i.e. high selectivity.

It is known that the selectivity of these catalysts tends to decrease after they have been used for a number of years. This decrease in selectivity results in less favorable economy of operation and may become of such magnitude as to render further operation with deteriorated catalysts totally uneconomical. Deteriorated catalysts may be replaced with fresh catalysts or may be regenerated. It is advantageous to replace or regenerate catalysts since an increase in selectivity of as little as one percentage point (selectivity = 100 × the amount of ethylene converted to ethylene oxide divided by the total ethylene consumed) will result in the savings of many thousands of dollars in a commercial operation. Regeneration is preferable to replacement since the former is significantly less expensive and less time consuming.

There are several known procedures for regenerating or reactivating used silver-based catalysts. U.S. Pat. No. 4,051,068 issued Sept. 27, 1977, U.S. Pat. No. 4,123,385 issued Oct. 31, 1978, U.S. Pat. No. 4,125,480 issued Nov. 14, 1978, and U.S. Pat. No. 4,177,169 issued Dec. 4, 1979 describe four such methods for regenerating silver catalysts. All four methods involve applying to the spent or used catalysts a regenerant such as a cesium or rubidium compound such that the concentration of the regenerant is in the range of 1 to 1,000 parts per million. This is generally achieved by contacting the used catalyst with a solution of the regenerant in an inert solvent. In the first, second and fourth patents, drying is accomplished by evaporation at 50° to 100° C. although lower temperatures can be used if a vacuum is applied to the catalyst. They all say that this evaporation process can optionally be accomplished while blowing nitrogen through the catalyst. The third patent accomplishes drying by heating at 50° to 200° C. or, preferably, purging the catalyst with a gas stream at 15° to 200° C. None of these patents mention upflow drying or the increase in productivity which can be obtained if upflow drying is used.

SUMMARY OF THE INVENTION

The present invention relates to a method for regenerating a supported silver catalyst which has been used for the direct oxidation of ethylene to ethylene oxide. The method comprises applying to the catalyst from 1 to 1,000 parts per million of a regenerant which can be selected from the group consisting of salts of alkali metals, such as cesium, rubidium, and mixtures thereof. The regenerant is applied by treating the catalyst with a solution of the regenerant in an inert liquid. The final step of the process is drying the catalyst by passing an inert gas upwardly through the catalyst at a temperature below the boiling point of the inert liquid. Ambient temperature is preferred. It is preferred that the drying step be continued until the concentration of the inert liquid in the exiting gas stream is less than 0.1%. It is also preferred that the flow rate of the inert gas be from about 0.1 to about 30 liters per minute per square centimeter of cross sectional area of the catalyst bed. It is most preferred to operate at 0.5 to 1.5 l/min./cm$^2$.

DETAILED DESCRIPTION OF THE INVENTION

The catalyst may be regenerated according to the processes of any of the aforementioned patents. In general, the catalyst is contacted with a solution of a regenerant in a liquid which is inert with respect to the catalyst. The contacting can be accomplished by immersing the catalyst in the solution, by causing the solution to flow through the catalyst in a closed container, or by any other convenient method as long as sufficient regenerant is applied to the catalyst. In the case of alkali metal salts, 1 to 1,000 parts per million is sufficient. Deposition of the optimum concentration of regenerant on the catalyst bed can be achieved by soaking the catalyst for a period of 1 to 4 hours in the regenerant solution, draining for a period of 5 to 60 minutes, and then drying as described below.

Suitable regenerant compounds are, for example, the hydroxides, nitrates, chlorides, iodides, bromides, bicarbonates, and carbonates of alkali metals, especially cesium and rubidium, or organic derivatives thereof, for example, their alkoxides, such as the isopropoxides, or their salts with organic carboxylic acids, such as, for example, the acetates, oxalates, tartrates, lactates, formates, and propionates. Organic compounds are preferred for use as the inert liquid. Suitable inert liquid solvents are, for example, alkanols having 1 to 6 carbon atoms such as, for example, methanol, ethanol, and isopropanol, and aliphatic, alicyclic, or aromatic hydrocarbons, ethers, and ketones. Aliphatic or aromatic amides and aldehydes can also be used, as well as nitriles. The alcohols are preferred but acetone, methylacetate, tetrahydrofuran, and acetronitrile can also be used with highly advantageous results. The choice of the solvent for regeneration appears to be dictated only by the drying time available. Methanol has the highest vapor pressure of the aliphatic alcohols and is thus preferred as the solvent for this process because it minimizes drying time and total gas flow. For purposes of this invention, the concentration of water in the regeneration solution is to be preferably less than 1% and more particularly less than 0.1%. Better results are obtained when the water level is kept low.

I have found that it is critical for achieving optimum catalyst performance following regeneration that the drying step of the process consist of passing an inert gas upwardly through the catalyst. By application of the procedure described below, superior catalyst performance can be attained.

The inert gas used to flow upwardly through the catalyst can be nitrogen, argon, any other noble gas, methane, ethylene, air, or any gas which is not reactive under the conditions specified, but preferably is clean air or nitrogen because they are inexpensive and not environmentally harmful. Application of a vacuum during the drying process should be avoided. The drying process should be carried out below the boiling point of the inert liquid and preferably at ambient temperature. The flow rate of the inert gas through the catalyst should be in the range of 0.1 to 30 liters per minute per square centimeter of cross sectional area of catalyst bed. The rate should be in the range of 0.5 to 1.5 l/min./cm² to achieve effective drying at a practically achievable flow rate.

By using the drying step described above, better catalyst performance can be obtained. Specifically, the selectivity of the catalyst can be increased. The selectivity of the regenerated catalyst is higher if the regenerant is evenly dispersed throughout the catalyst bed. The purpose of the present drying step is to dry the catalyst without disturbing the even dispersal of the regenerant. Downflow drying is to be avoided because it has a tendency to propel the regenerant solution down through the catalyst resulting in large deviations in regenerant concentration from the optimum. Upflow drying minimizes the weeping or dripping of the regenerant solution down through the catalyst bed.

Heating during the drying step to a temperature near or above the boiling point of the inert liquid is to be avoided because this also results in concentration variations in the catalyst because if the solvent vaporizes quickly, the promoter will, in part, be forced off of the catalyst. Also, if boiling takes place at one point in the tube, but not at others, the solvent will condense at the cooler points and dilute the regenerant at those points. Ambient temperature is preferred because it minimizes the chances of recondensation of the solvent and dilution of the regenerant.

The application of a vacuum to assist the drying process is to be avoided as this appears to increase the tendency for the regeneration to be unevenly dispersed throughout the catalyst bed. It is preferred that the drying process be continued until the concentration of the inert liquid in the outlet gas stream is 0.1% or lower because for all practical purposes, the catalyst is sufficiently dry at that point.

EXAMPLES

Samples of a silver-based catalyst that had been used for many years for the production of ethylene oxide were used for the following three experiments. Whole tube samples of the ethylene oxide catalyst were withdrawn from the same reactor. Each tube was divided into five equal sections upon removal and was reloaded in a test reactor with the same relative alignment of the sections.

The test reactor consisted of a 1-inch tube with a 24-foot length of catalyst bed. A performance evaluation of the individual tubes was conducted prior to regeneration. The catalyst was operated in the temperature range of 450°–500° F. and used to make ethylene oxide with a process stream consisting of 18% ethylene, 7% oxygen, 5% carbon dioxide, and the balance nitrogen with from 30 to 250 parts per million of ethylene dichloride added as an inhibitor. The three samples of catalyst were found to have selectivities in the range of 67%–68%.

After the baseline data was collected on each catalyst sample, the samples were each treated with a regeneration solution prepared from 0.352 grams of cesium carbonate ($Cs_2CO_3$), 0.15 milliliters of acetic acid, and 2.5 liters of methanol. The acetic acid was added as a solubilizing agent to aid in dissolving the cesium carbonate. This clear solution was pumped into the catalyst bed from the bottom upwardly until the entire tube was full of regeneration solution. The solution was allowed to contact the catalyst for 2 hours, drained in 15 minutes, and allowed to stand for 30 minutes. Drying was then begun under the individual conditions detailed below.

Catalyst sample A was dried by flowing nitrogen at 0.91 liters per minute per square centimeter upwardly through the catalyst bed for 14 hours at ambient temperature. Catalyst sample B was dried by flowing nitrogen at 0.85–0.91 liters per minute per square centimeter upwardly through the catalyst bed. Drying initiated at ambient temperature but the temperature was raised at a rate of 25°–30° C. per hour until a temperature of 100° C. was achieved (approximately 3 hours). Drying was continued at this temperature for 1 additional hour at which time drying was discontinued by stopping the gas flow and removing the heat. Catalyst sample C was dried entirely at ambient temperature by flowing the nitrogen stream downwardly through the catalyst bed at 0.85–0.91 liters per minute per square centimeter for 14 hours.

The dried catalysts were then evaluated by using them to make ethylene oxide under the same process and conditions described above. The selectivity of catalyst A was increased by 3.6 points, the selectivity of catalyst B was increased 2.6 points, and the selectivity of catalyst C was increased by 2.8 points. It can be seen that the method of the present invention, as exemplified by catalyst A, achieves significantly higher improvement in catalyst efficiency (selectivity) than does upflow drying at elevated temperature or downflow drying.

The catalysts were removed from the reactor in 5 equal sections. Sample 1 was taken from the bottom of the reactor tube and so on up to Sample 5 which was taken from the top. Each section was analyzed for promoter concentration and the results are set out in Table 1 below.

TABLE 1

| Catalyst | Sample | Cs Concentration (ppm) |
|---|---|---|
| A | 1 | 27 |
|   | 2 | 30 |
|   | 3 | 25 |
|   | 4 | 25 |
|   | 5 | 26 |
| B | 1 | 27 |
|   | 2 | 20 |
|   | 3 | 17 |
|   | 4 | 14 |
|   | 5 | 13 |
| C | 1 | 27 |
|   | 2 | 21 |
|   | 3 | 22 |
|   | 4 | 19 |
|   | 5 | 19 |

It is clear that the dispersion of the regenerant on catalyst A is much more even than the dispersion on either catalyst B or C. Thus, it can be seen that the method of the present invention provides a more even dispersion of the regenerant solution on the catalyst than the other two methods.

I claim:

1. A method for regenerating a supported silver catalyst which has been used for the direct oxidation of ethylene to ethylene oxide which comprises applying to the catalyst an effective amount of a regenerant by treating the catalyst with a solution of the regenerant in an inert liquid and then drying the catalyst by passing an inert gas upwardly through the catalyst at a temperature below the boiling point of the inert liquid.

2. The method of claim 1 wherein the regenerant is selected from the group consisting of alkali metal salts.

3. The method of claim 2 wherein the alkali metal salt is selected from the group consisting of cesium, rubidium and mixtures thereof.

4. The method of claim 2 wherein from 1 to 1,000 parts per million of the regenerant is applied to the catalyst.

5. The method of claim 1 wherein the drying is carried out at ambient temperature.

6. The method of claim 1 wherein the drying step is continued until the concentration of the inert liquid in the exit gas stream is less than 0.1%.

7. The method of claim 1 wherein the flow rate of the inert gas is from about 0.1 to about 30 liters per minute per square centimeter of cross section of catalyst bed.

8. The method of claim 7 wherein the flow rate of the inert gas is from about 0.5 to about 1.5 liters per minute per square centimeter of cross section of catalyst bed.

9. In a method for regenerating a supported silver catalyst which has been used for the direct oxidation of ethylene to ethylene oxide which comprises applying to the catalyst an effective amount of a regenerant by treating the catalyst with a solution of the regenerant in an inert liquid and then drying the catalyst, the improvement which comprises drying the catalyst by passing an inert gas upwardly through the catalyst at a temperature below the boiling point of the inert liqiud.

10. The method of claim 9 wherein the regenerant is selected from the group consisting of alkali metal salts.

11. The method of claim 10 wherein the alkali metal salt is selected from the group consisting of cesium, rudidium and mixtures thereof.

12. The method of claim 10 wherein from 1 to 1,000 parts per million of the regenerant is applied to the catalyst.

13. The method of claim 9 wherein the drying is carried out at ambient temperature.

14. The method of claim 9 wherein the drying step is continued until the concentration of the inert liquid in the exit gas is less than 0.1%.

15. The method of claim 9 wherein the flow rate of the inert gas is from about 0.1 to about 30 liters per minute per square centimeter of cross section of catalyst bed.

16. The method of claim 15 wherein the flow rate of the inert gas is from about 0.5 to about 1.5 liters per minute per square centimeter of cross section of catalyst bed.

* * * * *